United States Patent [19]

Taylor et al.

[11] Patent Number: 4,505,924

[45] Date of Patent: Mar. 19, 1985

[54] PHARMACEUTICAL PREPARATION FOR THE TOPICAL TREATMENT OF ACNE

[75] Inventors: Peter Taylor, Windlesham; Alan A. Levy, Stanmore, both of England

[73] Assignee: Richardson-Vicks Ltd., Great Britain

[21] Appl. No.: 482,420

[22] Filed: Apr. 6, 1983

[30] Foreign Application Priority Data

May 3, 1982 [EP] European Pat. Off. ........ 82103791.8

[51] Int. Cl.³ .................. A61K 31/255; A61K 31/415
[52] U.S. Cl. ..................................... 514/399; 514/859
[58] Field of Search ........................... 424/273 R, 303

[56] References Cited

U.S. PATENT DOCUMENTS

| | | | |
|---|---|---|---|
| 3,687,855 | 8/1972 | Halpern | 424/150 X |
| 4,398,045 | 8/1983 | Sebag | 424/365 X |
| 4,401,712 | 8/1983 | Morrison | 424/33 X |

OTHER PUBLICATIONS

Merck Index, 9th Ed., 1976, p. 615; #4562.

*Primary Examiner*—Leonard Schenkman
*Attorney, Agent, or Firm*—George W. Rauchfuss, Jr.; Salvatore R. Conte

[57] ABSTRACT

A pharmaceutical preparation for the topical treatment of acne is disclosed comprising a combination of Imazilil and Hexamidine as essential active substances. This combination shows antimicrobial activity higher than that of the individual substances.

13 Claims, No Drawings

PHARMACEUTICAL PREPARATION FOR THE TOPICAL TREATMENT OF ACNE

FIELD OF THE INVENTION

Acne is a common inflammatory pilobaceous disease characterized by comedones, papules, pustules, inflamed nodules, superficial pus-filled cysts, and in extreme cases, sinus formation and deep inflammation, sometimes associated with prurulent sacs.

The pathogenesis of acne is complex. An interaction between hormones, keratinization, sebum and bacteria somehow determines the course and severity of the disease. Acne begins at puberty when the increase of androgens causes an increase in the size and activity of the pilosebaceous glands. The earliest microscopic change is intrafollicular hyperkeratosis, which leads to restriction of the pilosebaceous follicle with consequent formation of the comedo composed of sebum, keratin, and microorganisms, particularly *Propionibacterium* (*Corynebacterium*) *acnes*. Lipases from *P. acnes* break down triglycerides in the sebum to form free fatty acids (FFA), which irritate the follicular wall. Retention of sebaceous secretions and dilation of the follicle may lead to cyst formation. Rupture of the follicle with release of the contents into the tissues induces an inflammatory reaction which heals with scarring in severe cases.

Acne tends to appear during puberty and to fade away again, usually spontaneously when growth has stopped. Only rarely does it recede before the age of 20, and occasionally it is still to be found at the age of 30 and beyond. Since the face is the favorite location affected and in severe cases the alterations cause considerable disfigurement, they are aestheticaly very important and make the physical burden of the afflicted person easy to understand.

PRIOR ART

For the treatment of acne, warm wash with Syndets is recommended followed by a localized treatment with, for example, sulphur, resorcinol, salicylic acid, benzoyl peroxide or vitamin A acids.

The use of antibiotics like tetracycline and erythromycin is described in Brit. J. of Dermatology (1981) 104, P. 453–456. Furthermore, hexamidine isethionate and aluminum lactate in isopropanol are known to be used for the treatment of acne.

All the known preparations have one or more disadvantages, particularly lack of effectiveness. Accordingly, the cure rate with vitamin A acids is between 25 and 30%. This low rate of good results is due not only to the poor stability of vitamin A acids but also to undesirable and distressing side effects.

DISCLOSURE OF THE INVENTION

Thorough research of the pharmacological properties of 1-[2-(2,4-dichlorophenyl)-2-(2-propenyloxy)ethyl]-1H-imidazole (Imazalil) and 4,4-(hexamethylene (dihydroxy)-dibenzamidine-di-$\beta$-hydroxy ethanesulfonate (hexamidine diisethionate, hereinafter called Hexamidine) has revealed the surprising finding that the combination of Imazalil and hexamidine isethionate has a synergistic effect on reducing the physiological parameters associated with acne vulgaris.

The object of the invention thus is to provide a pharmaceutical preparation cointaining Imazalil or its acid addition salt in combination with Hexamidine for the local treatment of acne. A further object of the invention is to provide a method for the topical treatment of acne with a potent anti-acne preparation.

Studies using a chemostat revealed that Imazalil and Hexamidine could reduce the production and activity of exoenzymes of Propionibacterium acnes at sublethal levels. The enzymes are believed to play a role in the pathogenesis of acne. Imazalil is a direct lipase inhibitor and also reduces the production of hyaluronidase and acid phosphatase. Hexamidine likewise reduces the lipase activity.

The combination of Imazalil with hexamidine according to this invention in an anti-acne preparation for topical use has been shown to possess the following attributes:

1. The activity of the combination is higher than that of the individual substances (synergism).
2. Anti-enzymatic activity vs. *P. acnes* exoenzymes.
3. No deactivation by skin lipids.
4. Skin substantivity.
5. Antimicrobial activity against aerobic and anaerobic bacteria and fungi associated with acne.
6. Reduction in FFA levels.
7. Good sebum absorption properties.

Suitable examples of Imazalil acid addition salts are the sulfate and nitrate. Imazalil base is preferred.

The ratio of Imazalil to Hexamidine is not particularly limited, it may vary in a preferred range of about 1000:1 and about 2:1 parts by weight. A more preferred range would be a ratio of about 100:1 to about 2:1 parts by weight. The most preferred range being the ratio of about 10:1 parts by weight. The combination of 1.0% Imazalil with 0.1% Hexamidine in a pharmaceutical preparation is specially preferred.

Thus it was shown that the combination of 20 $\mu$g/ml Imazalil and 2 $\mu$g/ml Hexamidine totally inhibited the lipase production and reduced the hyaluronidase output by 50% and the acid phosphatase output by 80%.

Pharmaceutical preparations for topical use of this invention can be prepared in a manner known in the art, using conventional carriers and auxiliary agents, e.g. emulsifiers, emollients, thickening agents, solvents, coloring agents, perfumes and antifoaming agents.

Suitable emulsifiers can be anionic, cationic or non-ionic emulsifiers. Typical examples of anionic emulsifiers are the salts of aliphatic acids of the general formula RCOOX where R is an aliphatic hydrocarbon group of about 6 to 24 carbon atoms and X is for instance sodium, potassium or triethanolamine etc., such as sodium stearate.

Cationic emulsions can for example be prepared using aliphatic amides such as diethylaminoethyl stearamide, and quaternary ammonium compounds such as cetrimide.

Especially preferred non-ionic emulsifiers are polyoxyethylene aliphatic acid esters of the general formula R—CO—O(CH$_2$CH$_2$O)$_n$H where R is an aliphatic hydrocarbon group containing 4 to 24 carbon atoms and n is 2–150 (e.g. polyethylene glycol 1000 monostearate), and partial esters of a polyhydric alcohol containing 2 or 6 carbon atoms (e.g. glyceryl monostearate).

Suitable emollients include aliphatic alcohols containing 4 to 20 carbon atoms and polymers of these glycols (e.g. polyethylene glycols such as PEG 400). Fatty acids containing 6 to 24 carbon atoms can be used (e.g. stearic acid) as well as aliphatic esters of the general formula $R_1COOR_2$ where $R_1$ and $R_2$ may each contain 1 to about 22 carbon atoms (e.g. isopropyl myristate).

As suitable thickening agents, hydrated aluminum silicates, e.g. bentonites, and carboxyvinyl polymers (e.g. Carbopol) may be used. Cellulose gums such as sodium carboxymethyl cellulose and especially mixtures with microcrystalline cellulose are preferred (e.g. Avicel RC grades).

Suitable solvents are lower aliphatic alcohols containing 1 to 4 carbon atoms e.g. methanol, ethanol and propanol.

The pharmaceutical preparation may also contain coloring agents or inorganic pigments, perfumes and antifoaming agents, examples being titanium dioxide, menthol and silicone fluids, and sulphur.

Studies have shown that the chemical nature of the cream base is an important factor in the overall activity of the final preparation. A very effective cream base is a non-ionic isopropyl myristate/cetyl alcohol emulsion. This formulation is substantive to the skin and antimicrobial activity can be detected on subjects 24 hours after application. The cream formulation significantly reduces levels of S.epidermidis and P.acnes on the skin surface after 2 weeks' use. There is also a highly significant reduction in free fatty acid levels on the skin, indicating a reduction of lipolytic activity.

The following formulations are typical for the manufacture of pharmaceutical preparations of the invention.

| Formulation 1 (cream) | % w/w |
|---|---|
| Isopropyl myristate | 3.00 |
| Cetyl alcohol | 2.00 |
| PEG 1000 monostearate | 2.50 |
| Avicel | 7.50 |
| PEG 400 | 5.00 |
| Sulphur | 5.00 |
| Hexamidine isethionate | 0.10 |
| Imazalil | 1.00 |
| Pigment | 0.10 |
| Perfume | q.s. |
| Ethanol | 10.83 |
| Water q.s. | 100.00 |

Note: PEG = Polyethylene glycol

Manufacture of the cream:

The Hexamidine is dissolved by heating in the water phase and then emulsified by hot addition of the oil phase consisting of isopropyl myrisate, PEG 1000 monosterate and cetyl alcohol, the Avicel and sulphur are then added and mixing is continued until the temperature is below 30° C. then the Imazalil, PEG 400, perfume and pigments are dispersed in the alcohol and this solution is added to the bulk which is mixed until homogeneous.

| Formulation 2 (gel) | % w/w |
|---|---|
| Imazalil | 1.00 |
| Triton X 100 (octyl phenoxy polyethoxy ethanol) | 1.50 |
| Simethicone (polydimethylsiloxane) | 1.00 |
| Carbopol gel | 53.70 |
| Triethanolamine | 0.81 |
| Ethanol | 34.20 |
| Hexamidine isethionate | 0.10 |
| Color | q.s. |
| Demineralised water | 7.58 |

Manufacture of the gel:

Both alcohol and dye are added to the aqueous acid dispersion of Carbopol and mixed until homogeneous. The Hexamidine is dissolved in water by warming to 50° C. and then added to the Carbopol dispersion. The mixture is neutralized by the addition of triethanolamine and mixed to give a gel.

The Imazalil is dissolved in the Triton X 100 and Simethicone and heated to 70° C. Perfume is added and this solution is then mixed with the gel to give a clear gel.

The following tests results illustrate essential attributes of the Imazalil-Hexamidine alone and the combination in pharmaceutical preparations for the topical treatment of acne. These include various cream formulations and a gel.

1. Anti-enzymic Properties of Imazalil and Hexamidine

Imazalil and Hexamidine have been studied for anti-enzymic properties against the production and activity of the exoenzymes of Propionibacterium acnes. Using continuous culture techniques, the following properties of the antimicrobials have been demonstrated.

(a) Imazalil
(i) Imazalil directly inhibited lipase activity. There was a 29% reduction of lipase activity in the presence of 10 µg/ml Imazalil and a 68% reduction with 100 µg/ml Imazalil.
(ii) Imazalil reduced the output of hyaluronidase and acid phosphatase by P.acnes.

Levels of hyaluronidase fell by 50% after growth in the presence of 10 µg/ml Imazalil. Production of acid phosphatase was totally inhibited.

(b) Hexamidine
(i) A leval of 1 µg/ml Hexamidine reduced lipase activity by 33%.

(c) Imazalil and Hexamidine
(i) 100 µg/ml Imazalil and 1 ug/ml Hexamidine reduced lipase activity by 55%.
(ii) Production of lipase, hyaluronidase and acid phosphatase was markedly affected by a mixture of 10 µg/ml Imazalil and 1 µg/ml Hexamidine. Lipase output was totally inhibited. Hyaluronidase output was reduced by 50%. Acid phosphatase output was reduced by 80%.

2. Resistance to Inactivation by Sebum
(i) A zone diffusion test using 1% artificial sebum in agar seeded with P. acnes revealed that Imazalil was partially inhibited by lipids whereas Hexamidine was totally resistant to the inhibitive effect.

|  |  | Zone of Inhibition mm | |
|---|---|---|---|
|  |  | Control | Sebum |
| Imazalil | 10 µg | 0 | 0 |
| Imazalil | 100 µg | 5.0 | 1.5 |
| Hexamidine | 10 µg | 9.0 | 11.0 |
| Hexamidine | 100 µg | 31.5 | 33.0 |

(ii) The test was repeated using 0.2 ml of cream. The overall activity of the cream was unaffected by the lipids.

|  | Zone of Inhibition mm | |
|---|---|---|
|  | Control | Sebum |
| Formulation 1 | 39.0 | 38.0 |

3. Skin Substantivity

The antimicrobial activity retained on the skin was determined using the seeded plate method of Eigen et al., Cosmet. Toil. 92, 47, 1977. The skin was sampled 0, 4, 16 and 24 hours after application of the emulsion system of formulation 1. The reductions in numbers of the test organism, *S. epidermidis,* were as follows:

| Time After Application | % Reduction |
|---|---|
| 0 hour | 100% |
| 4 hours | 100% |
| 16 hours | 100% |
| 24 hours | 99.9% |

High activity was retained on the skin for at least 24 hours.

4. Activity of Imazalil and Hexamidine Against Bacteria Involved in Acne

The combination of Imazalil and Hexamidine showed a broad spectrum of activity against skin bacteria and yeasts.

| (i) Zone Diffusion Test | | | | |
|---|---|---|---|---|
| | | Zone of Imhibition mm | | |
| | | P. acnes | S. epidermidis | Pi. ovale |
| Imazalil | 10 μg | 3 | 3 | 11 |
| Imazalil | 80 μg | 22 | 7.5 | 28 |
| Hexamidine | 20 μg | 17 | 10 | — |
| Hexamidine | 20 μg | 22.5 | 13 | — | ii. Two in vitro studies revealed that daily application of the cream to the forehead significantly reduced the levels of aerobic and anarobic skin bacteria. Slightly lower activity was demonstrated by using the gel.

5. Reduction in Free Fatty Acid Levels

Free fatty acid determinations were carried out during the previous in vitro studies. Application of the cream caused an overall reduction of 30% in the fatty acid content of skin surface lipids. Tests using the gel revealed activity of a similar order.

6. Combination of Imazalil/Hexamidine: Synergistic Effect

Imazalil and Hexamidine were tested for synergistic activity using a zone diffusion test. The results revealed that when the concentration of Imazalil exceeded that of Hexamidine, there was a synergistic effect. When the concentrations were equal, there was evidence of slight antagonism.

| | Zone mm | Effect |
|---|---|---|
| Imazalil 10 μg | 0 | |
| Imazalil 100 μg | 5.5 | |
| Hexamidine 1 μg | 3.0 | |
| Hexamidine 10 μg | 10.0 | |
| Hexamidine 100 μg | 29.5 | |
| Imazalil 10 μg + Hexamidine 1 μg | 7.5 | synergism |
| Imazalil 100 μg + Hexamidne 1 μg | 18.0 | synergism |
| Imazalil 10 μg + Hexamidine 10 μg | 8.5 | slight antagonism |
| Imazalil 100 μg + Hexamidine 10 μg | 28.5 | synergism |
| Imazalil 10 μg + Hexamidine 100 μg | 30.5 | due to Hexamidine only |
| Imazalil 100 μg + Hexamidine 100 μg | 30.5 | due to Hexamidine only |

7. Sebum Asorption Properties

In vitro sebum absorption experiments using the formulation 1 demonstrated good sebum absorption properties when the absorbed sebum was monitored by gas chromatography.

8. Activity in Anionic, Non-Ionic and Cationic GMS Emulsions

To test the effect on the activity of Imazalil and Hexamidine, three simple emulsions containing the following grades of glycerol monostearate were prepared:

| anionic: | 5% GMS SE |
|---|---|
| non-ionic: | 10% Cerasynt 945 |
| cationic: | 7.5% Lexamul AR |

The emulsions were tested for in vivo activity using a seeded plate test. At 0 and 4 hours on the skin, total inhibition was achieved with all three emulsions. At 16 hours and 24 hours differences began to emerge.

| | % Reduction |
|---|---|
| 16 Hours | |
| anionic | 81% |
| non-ionic | 99% |
| cationic | 95% |
| 24 Hours | |
| anionic | 58% |
| non-ionic | 81% |
| cationic | 56% |

The non-ionic system appeared to be most effective at inhibiting the test organism, particularly at 24 hours on the skin.

A zone diffusion test was carried out on the three emulsions. The results were as follows:

| | Zone mm | |
|---|---|---|
| | P. acnes | S. epidermidis |
| anionic | 17 | 15 |
| non-ionic | 35.5 | 17.5 |
| cationic | 32.5 | 18 |

9. Activity in Anionic, Non-Ionic and Cationic IPM/Cetyl Alcohol Emulsions

A further three simple emulsions were prepared with IPM and cetyl alcohol. The anionic system contained stearic acid as an emulsifier, the cationic contained sapamine and the non-ionic contained PEG 1000 monostearate.

A seeded plate test revealed that the three formulations were equally effective and almost 100% inhibition of the test organism occured after the products had been on the skin for 24 hours. The formulations were superior in activity to the GMS emulsions.

A zone diffusion est was carried out and revealed that the Isopropyl myristate/cetyl alcohol formulations were more active than the GMS emulsions. The ranking order for activity against *P. acnes* was the same as the GMS emulsions.

| | Mean Zone mm | |
|---|---|---|
| | P. acnes | S. epidermidis |
| anionic | 23.5 | 14 |
| non-ionic | 37.5 | 18 |
| cationic | 35.0 | 18 |

We claim:

1. A pharmaceutical preparation for the topical treatment of acne in humans comprising a pharmaceutically acceptable carrier and a synergistic combination of Imazalil or an acid addition salt thereof and hexamidine isethionate in the range of from approximately 100:1 to approximately 10:1 parts by weight respectively.

2. The preparation of claim 1 in which the ratio of Imazalil to hexamidine isethionate is in the range of about 10:1 parts by weight.

3. The preparation of claim 1 comprising Imazalil as a free base.

4. The preparation of claim 1 in which the carrier is a non-ionic cream base.

5. The preparation of claim 2 in which the carrier is a non-ionic cream base.

6. The preparation of claim 3 in which the carrier is a non-ionic cream base.

7. A method of treating acne vulgaris in a patient comprising topically applying to said patient an anti-acne effective amount of the pharmaceutical preparation of claim 1.

8. A method of treating acne vulgaris in a patient comprising topically applying to said patient an anti-acne effective amount of the pharmaceutical preparation of claim 2.

9. A method of treating acne vulgaris in a patient comprising topically applying to said patient an anti-acne effective amount of the pharmaceutical preparation of claim 3.

10. A method of treating acne vulgaris in a patient comprising topically applying to said patient an anti-acne effective amount of the pharmaceutical preparation of claim 4.

11. A method of treating acne vulgaris in a patient comprising topically applying to said patient an anti-acne effective amount of the pharmaceutical preparation of claim 5.

12. A method of treating acne vulgaris in a patient comprising topically applying to said patient an anti-acne effective amount of the pharmaceutical preparation of claim 6.

13. Pharmaceutical preparation comprising

|  | % w/w |
| --- | --- |
| Isopropyl myristate | 3.00 |
| Cetyl alcohol | 2.00 |
| PEG 1000 monostearate | 2.50 |
| Avicel | 7.50 |
| PEG 400 | 5.00 |
| Sulphur | 5.00 |
| Hexamidine isethionate | 0.10 |
| Imazalil | 1.00 |
| Pigment | 0.10 |
| Perfume | q.s. |
| Ethanol | 10.83 |
| Water, q.s. | 100.00. |

* * * * *